US012402969B2

(12) United States Patent
Beischel et al.

(10) Patent No.: US 12,402,969 B2
(45) Date of Patent: Sep. 2, 2025

(54) SURGICAL DRAPE SUPPORT

(71) Applicant: United States Government As Represented By The Department Of Veterans Affairs, Washington, DC (US)

(72) Inventors: Charles Beischel, Charleston, SC (US); Nicole Beitenman, Charleston, SC (US); Bethany Baldwin, Charleston, SC (US); David Gatlin, Charleston, SC (US); Jose Rodriguez, Charleston, SC (US)

(73) Assignee: United States Government as represented by the Department of Veterans Affairs, Washington, DC (US)

(*) Notice: Subject to any disclaimer, the term of this patent is extended or adjusted under 35 U.S.C. 154(b) by 196 days.

(21) Appl. No.: 18/454,373

(22) Filed: Aug. 23, 2023

(65) Prior Publication Data

US 2024/0065792 A1     Feb. 29, 2024

Related U.S. Application Data

(60) Provisional application No. 63/400,186, filed on Aug. 23, 2022.

(51) Int. Cl.
    *A61B 46/20*     (2016.01)
    *A61M 16/08*     (2006.01)
    *A61M 25/02*     (2006.01)

(52) U.S. Cl.
    CPC ......... *A61B 46/20* (2016.02); *A61M 16/0875* (2013.01); *A61M 2025/0213* (2013.01); *A61M 2025/024* (2013.01); *A61M 2202/0208* (2013.01)

(58) Field of Classification Search
CPC ......... A61B 46/20; A61B 46/10; A61B 46/00; A61B 2025/0213; A61B 2025/024; A61B 2046/205; A61B 90/40; A61B 90/05; A61M 16/0875; A61M 2202/0208; A61G 13/10; A47C 27/142
USPC .......................................... 128/849
See application file for complete search history.

(56) References Cited

U.S. PATENT DOCUMENTS

| | | | |
|---|---|---|---|
| 4,122,848 A | 10/1978 | Carpel | |
| 4,699,131 A * | 10/1987 | Crook | A61F 9/007 |
| | | | 128/206.28 |
| 6,302,109 B1 | 10/2001 | Parnes | |
| 2005/0005943 A1 | 1/2005 | Lanier | |

* cited by examiner

*Primary Examiner* — Alireza Nia
*Assistant Examiner* — Daniel A Miller
(74) *Attorney, Agent, or Firm* — Ballard Spahr LLP

(57) ABSTRACT

A surgical drape support for positioning on a patient's chest to support a drape above the patient's nose and mouth includes a main arch defining an inner main surface, an outer main surface, a main crown, a first main base edge, and a second main base edge. A first lower foot extends downward from the first main base edge and away from the outer main surface. A second lower foot extends downward from the second main base edge and away from the outer main surface. A first upper foot and a second upper foot extend upwards and away from the outer main surface to a position above the main crown. When the first lower foot and the second lower foot are positioned on the patient's chest they are configured to support the drape over the patient's nose and mouth.

20 Claims, 4 Drawing Sheets

SURGICAL DRAPE SUPPORT

CROSS-REFERENCE TO RELATED APPLICATION

This application claims priority to and the benefit of the filing date of U.S. Provisional Patent Application No. 63/400,186, filed Aug. 23, 2022, which is incorporated herein by reference in its entirety.

FIELD

This disclosure relates to a surgical drape support for maintaining a surgical drape properly positioned over a patient's nose and mouth. More specifically, the disclosure relates to a surgical drape support that is positionable on the patient's chest and configured to maintain proper orientation of the surgical drape during surgery.

BACKGROUND

The present disclosure describes a support for a surgical drape, for example, an ophthalmic drape and oxygen delivery system. An ophthalmic drape is required during eye surgery to provide a barrier between the patient and the operating surgeon. Ophthalmic drapes are typically placed over the patient and extend upwards on their body to their nose. Typically, only the eyes of the patient are exposed during the operation. A wide variety of methods have been used to support the ophthalmic drape including drape clips, IV poles, stretcher attachments, kidney basins, and even an auto repair funnel. However, many of these are complex, costly, difficult to install and adjust. In addition, many are not medical grade. The biggest challenge to present designs is proper adjustment such that the ophthalmic drape does not interfere with the patient's nose or mouth. Improper installation or insufficient support can result in limited spacing between the nose and mouth or excess spacing which can interfere with the surgeon's access to the eyes.

For some patients, the close proximity of a surgical drape to their nose and mouth may generate a feeling of claustrophobia and induce panic. Similarly, the attachment of an oxygen mask or cannula can exacerbate the feeling of claustrophobia. This is especially true for patients suffering from post-traumatic stress disorder. For these patients, a support that provides sufficient space and allows oxygen to be delivered to the cavity between the patient and the surgical drape, as opposed to attaching oxygen directly to the patient, would be highly desirable. It would also be highly desirable to have an inexpensive and easily adjustable support that is compatible with different body sizes.

DETAILED DESCRIPTION

Figure 1:
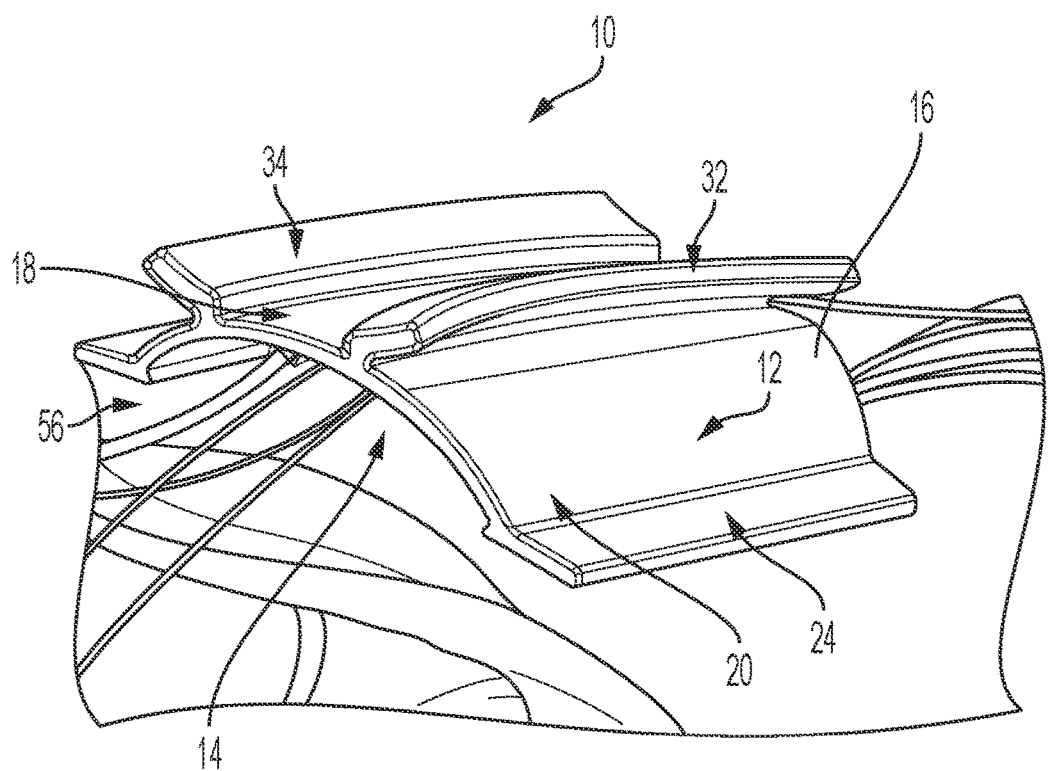
FIG. 1 is an isometric view of an example surgical drape support according to the disclosure.

The present disclosure can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

FIGS. 1-5 show surgical drape support 10 in accordance with one aspect of the present disclosure. The surgical drape support 10 includes a main arch 12 defining an inner main surface 14, an outer main surface 16, a main crown 18, a first main base edge 20, and a second main base edge 22. In one aspect of the disclosure, the main arch 12 comprises a semi-cylinder shape. The surgical drape support 10 further includes a first lower foot 24 extending downward from the first main base edge 20 and away from the outer main surface 16. In one aspect of the disclosure the first lower foot 24 is angled down relative to a plane generated by the first main base edge 20 and the second main base edge 22 by 10 to 30 degrees. The angle of the first lower foot 24 is configured to engage the chest 26 of a patient 28 (see FIG. 6). In one aspect of the disclosure, this comprises having the first lower foot 24 be at least slightly concave so conform to the patient's chest 26. Similarly, the surgical drape support 10 includes a second lower foot 30 extending downward from the second main base edge 22 and away from the outer main surface 16. In one aspect of the disclosure, the second lower foot 30 is a mirror of the first lower foot 24. In one aspect of the disclosure the second lower foot 30 is angled down relative to a plane generated by the first main base edge 20 and the second main base edge 22 by 10 to 30 degrees. The angle of the second lower foot 30 is configured to engage the chest 26 of a patient 28 (see FIG. 6). In one aspect of the disclosure, this comprises having second first lower foot 30 be at least slightly concave so conform to the patient's chest 26.

Figure 6:
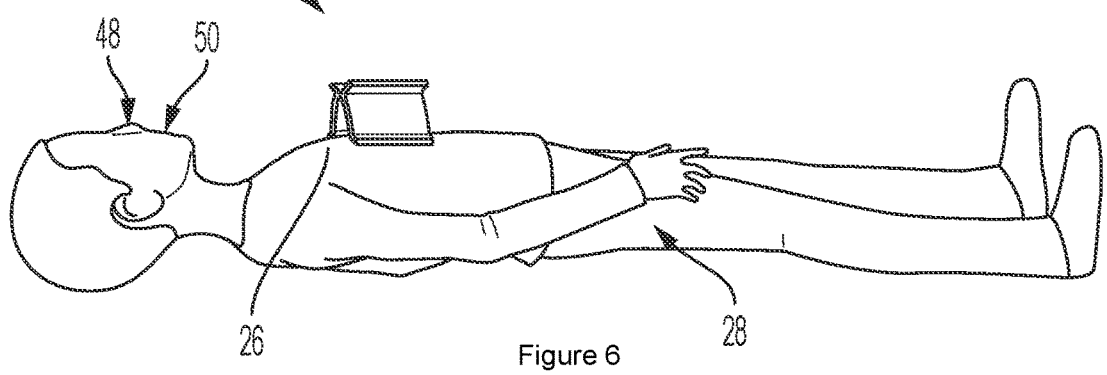
FIG. 6 is a side view of the surgical drape support shown in FIG. 1, the surgical drape support shown positioned on the patient's chest.
Figure 9:
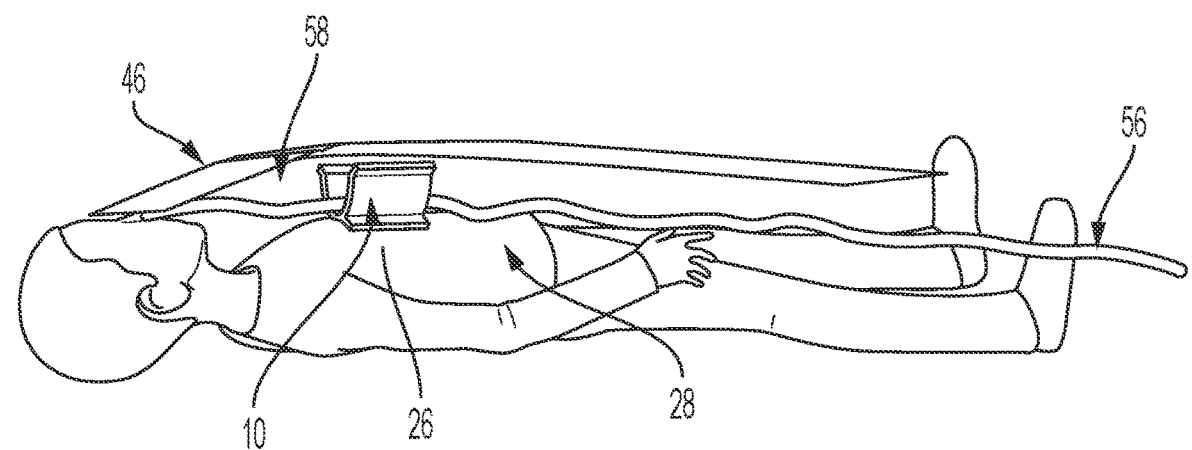
FIG. 9 is a side view of the surgical drape support shown in FIG. 1, the surgical drape support shown positioned on a smaller patient's chest and an ophthalmic drape overlaid on the patient and an oxygen supply attached.

The surgical drape support 10 may further include a first upper foot 32 extending upward and away from the outer main surface 16 to a position above the main crown 18. In one aspect of the disclosure the first upper foot 32 is angled upward relative to a plane generated by the first main base edge 20 and the second main base edge 22 by 10 to 30 degrees. The angle of the first upper foot 32 is configured to engage the chest 26 of a patient 28 (see FIG. 9). In one aspect of the disclosure this comprises having the first upper foot 32 be at least slightly concave when the first upper foot 32 is in contact with the patient's chest 26 (see FIG. 9). In another aspect of the disclosure, this comprises having the first upper foot 32 be at least slightly convex when the first lower foot 24 and the second lower foot 30 are in contact with the patient's chest 26 (FIG. 6). Similarly, the surgical drape support 10 may further include a second upper foot 34 extending upward and away from the outer main surface 16 to a position above the main crown 18. In one aspect of the disclosure, the second upper foot 34 is a mirror of the first upper foot 32. In another aspect, the second upper foot 34 is angled upward relative to the plane generated by the first main base edge 20 and the second main base edge 22 by 10 to 30 degrees. The angle of the second upper foot 34 is configured to engage the chest 26 of the patient 28 (see FIG. 9). In one aspect of the disclosure this comprises having the second upper foot 34 be at least slightly concave when the second upper foot 34 is in contact with the patient's chest 26 (see FIG. 9). In another aspect of the disclosure, this comprises having the second upper foot 34 be at least slightly convex when the first lower foot 24 and the second lower foot 30 are in contact with the patient's chest 26.

Figure 3:
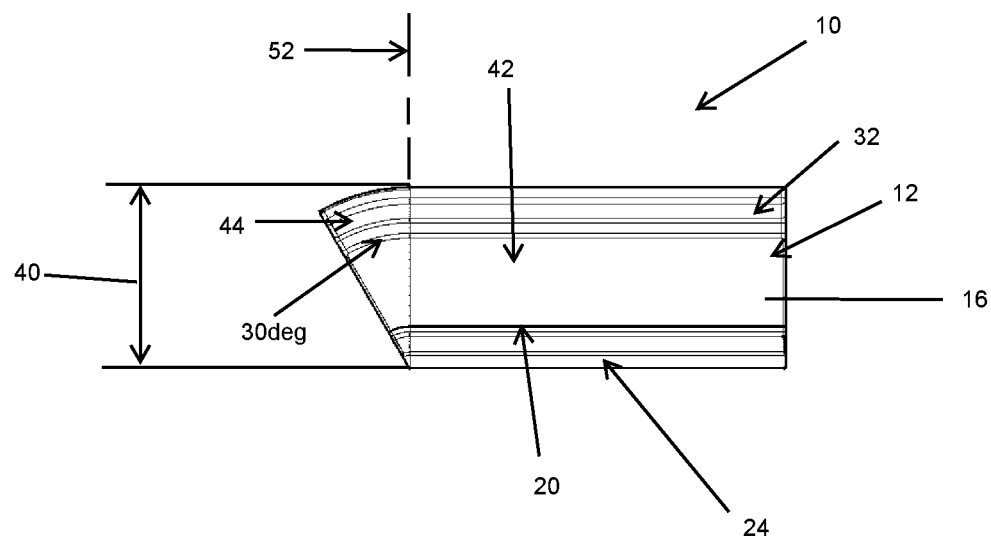
FIG. 3 is a side view of the surgical drape support shown in FIG. 1.
Figure 4:
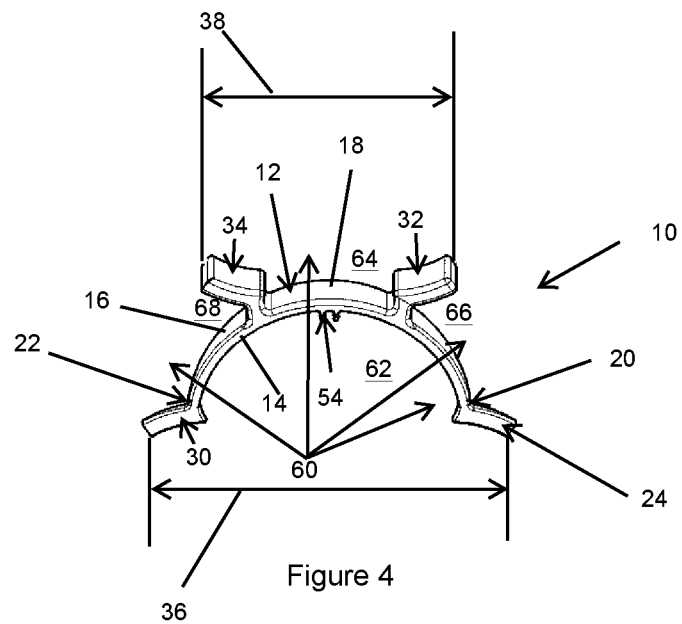
FIG. 4 is a front view of the surgical drape support shown in FIG. 1.
Figure 5:
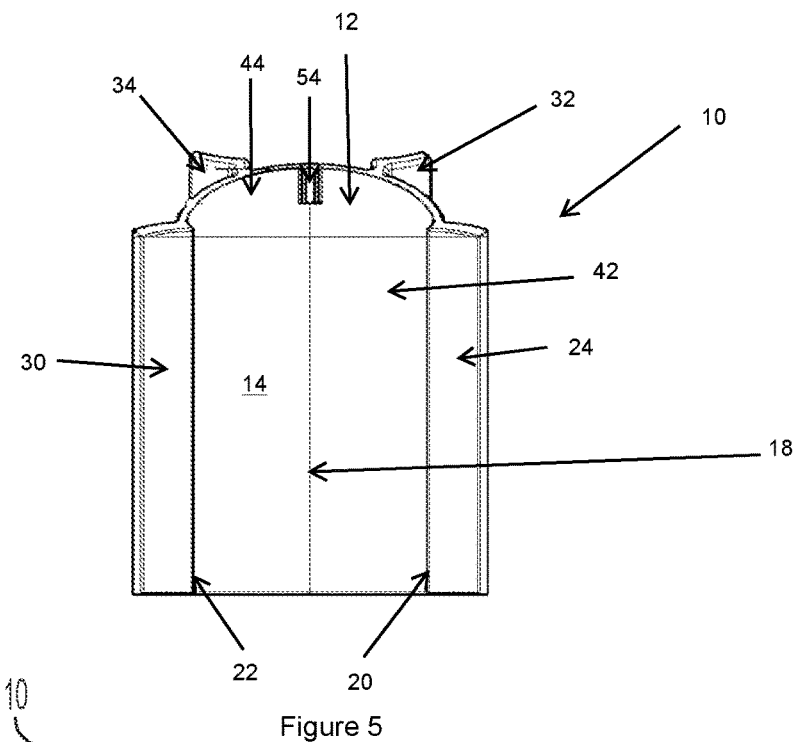
FIG. 5 is a bottom view of the surgical drape support shown in FIG. 1.
Figure 7:
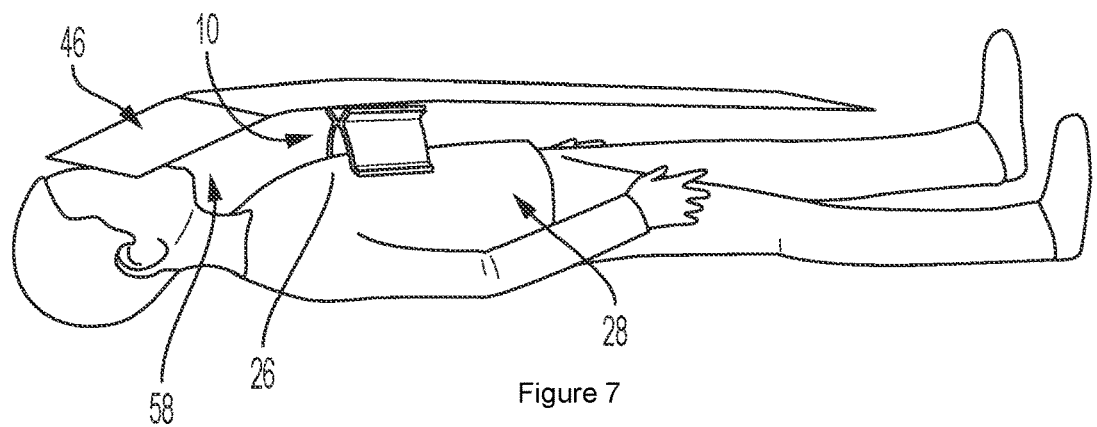
FIG. 7 is a side view of the surgical drape support shown in FIG. 1, the surgical drape support shown positioned on the patient's chest and an ophthalmic drape overlaid on the patient.
Figure 8:
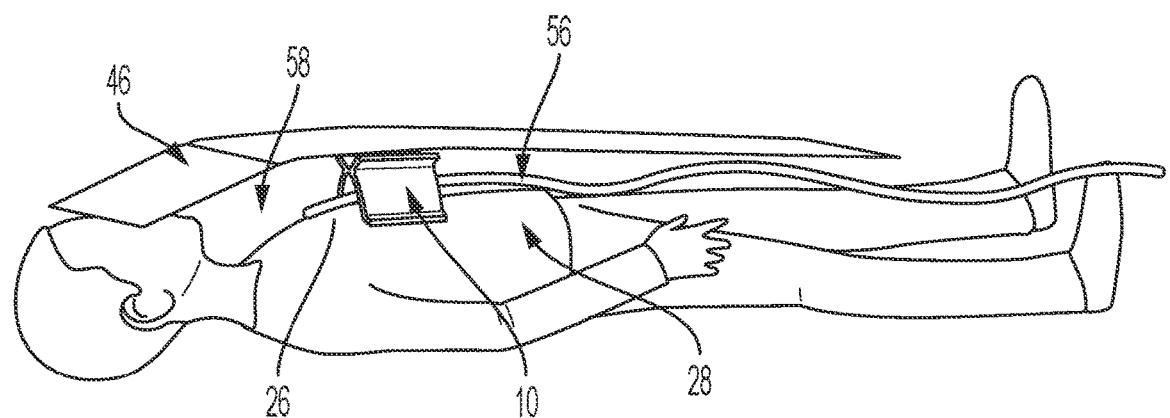
FIG. 8 is a side view of the surgical drape support shown in FIG. 1, the surgical drape support shown positioned on the patient's chest and an ophthalmic drape overlaid on the patient and an oxygen supply attached.

In one aspect of the disclosure, the first lower foot 24 and the second lower foot 30 define a lower foot width 36 (see FIG. 4). Similarly, the first upper foot 32 and the second upper foot 34 define an upper foot width 38. In one aspect, the upper foot width 38 is smaller than the lower foot width 36. This allows the surgical drape support 10 to be inverted between a position wherein the first lower foot 24 and second lower foot 30 are in contact with the patient's chest (FIGS. 6-8) when the patient 28 is larger to a position wherein the first upper foot 32 and the second lower foot 34 are in contact with the patient's chest 26 (FIG. 9) when the patient 28 is smaller. In one aspect, the lower foot width 36 is approximately 202 mm and the upper foot width 38 is approximately 138 mm. In another aspect, the lower foot width 36 is between 180 mm and 220 mm and the upper foot width 38 is between 118 mm and 158 mm. In still another aspect, the upper foot width 38 is approximately 70% of the lower foot width 36. Although specific dimensions and ranges are described, it is contemplated that the specific sizing of the lower foot width 36 and the upper foot width 38 may be tailored to the average sizes of larger and smaller patients 28. The main arch 12 defines a main arch height 40 (FIG. 3). In one aspect of the disclosure the main arch height 40 is approximately 85 mm. In another aspect, the main arch height 40 is between 40 percent and 50 percent of the lower foot width 36.

Figure 2:
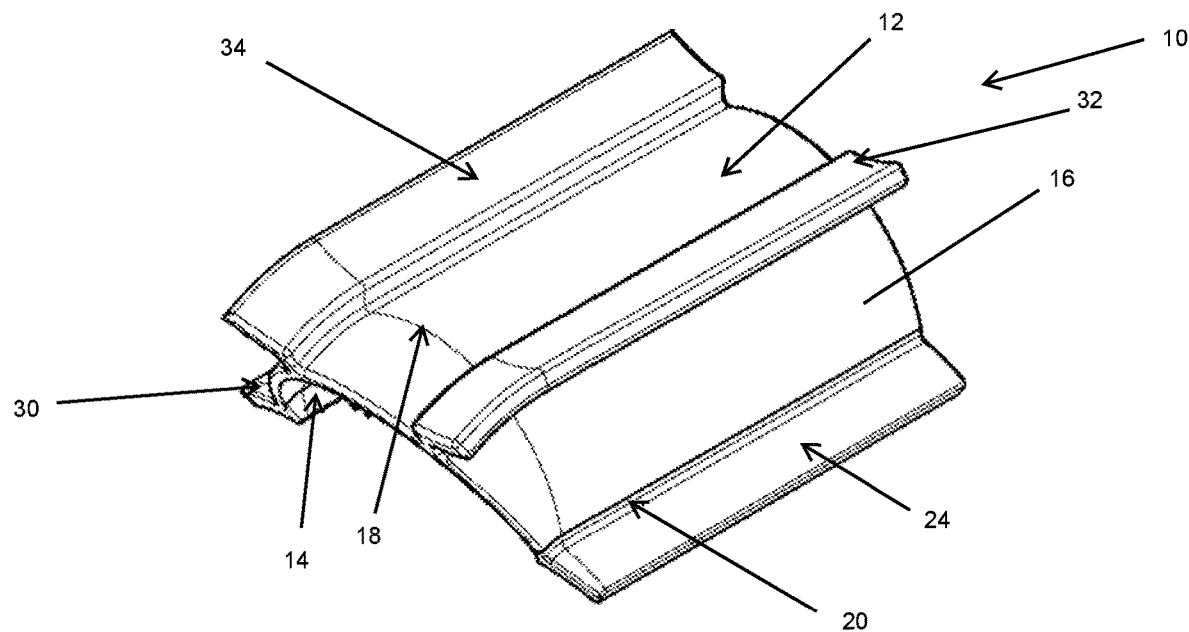
FIG. 2 is an isometric illustration of the surgical drape support shown in FIG. 1.

Although one aspect of the disclosure completes the use of a symmetrical surgical drape support 10, in another aspect shown in FIGS. 2 and 3 the surgical drape support 10 is comprised of a relatively symmetrical body portion 42 and a front lip portion 44. The front lip portion 44 is angled downward towards the plane defined by the first main base edge 20 and the second main base edge 22. In one aspect, the front lip portion 44 is angled (optionally, curved) downwards. In another aspect, the first upper foot 32 and the second upper foot 34 are curved or angled downward in the region of the front lip portion 44. The angling/curving of the front lip portion 44 helps guide an overlying surgical drape, in this example an ophthalmic drape 46, towards a position just above the patient's nose 48 and mouth 50 (See FIGS. 7 and 8) when the first lower foot 24 and the second lower foot 30 are positioned on the patient's chest 26. In one particular aspect of the disclosure, the front lip portion 44 is angled downwards (optionally, curved downwards) at an angle of 30 degrees from the vertical axis 52. In still another aspect, the front lip portion 44 only extends from the main crown 18 and not the first main base edge 20 or the second main base edge 22 (see FIG. 3). In other aspects, the front lip portion 44 may be angled based on the average size of a patient 28.

In another aspect of the disclosure, the surgical drape support 10 may include one or more accessory attachment features 54. The accessory attachment features 54 allow medical monitoring and oxygen delivery lines to be secured to the surgical drape support 10. In one aspect, at least one accessory attachment feature 54 is positioned on the inner main surface 14. One accessory attachment feature 54 is contemplated to be an oxygen hose clamp securing an oxygen line 56 (see FIG. 8). The surgical drape support 10, when placed on the patient 28 along with a surgical drape such as the ophthalmic drape 46, creates a cavity 58 where oxygen may be delivered without direct contact with the patient 28. This further minimizes stress on the patient 28. In other aspects, the oxygen may be delivered directly to the patient through a cannula or other delivery device (see FIG. 9). The surgical drape support 10 defines at least four accessory pathways 60 to route medical accessories to the patient 28. A main pathway 62 is defined through the main inner surface 14 of the main arch 12. A secondary pathway 64 is defined between the first upper foot 32 and the second upper foot 34. A first side pathway 66 is defined between the first lower foot 24 and the first upper foot 32. A second side pathway 68 is defined between the second lower foot 30 and the second upper foot 34. The use of multiple pathways allows accessories delivered to the patient 28 to be separated for organizational purposes. In addition, it allows accessories to be added or removed without disrupting accessories already installed.

Referring now to FIGS. 6-9, depicting an aspect of the current disclosure, the surgical drape support 10 is placed on the patient's chest 26 (see FIG. 6). A surgical drape, such as ophthalmic drape 46, is placed over the patient 28. The surgical drape support 10 is positioned such that the ophthalmic drape 46 is angled from the surgical drape support 10 to just above the patient's nose 48. The surgical drape support 10 can be moved up and down the patient's chest 26 until cavity 58 is sufficient for the comfort of the patient 28 while the angle of the ophthalmic drape 46 does not interfere with the surgeon's tools. If the patient's chest 26 is too small for the lower foot width 36, the surgical drape support 10 can be inverted such that the first upper foot 32 and the second upper foot 34 are in contact with the patient's chest 26. In at least one additional aspect of the disclosure, the first lower foot 24 and the second lower foot 30 as well as the first upper foot 32 and second upper foot 34 may be formed with a gripping pattern to prevent slippage of the ophthalmic drape 46. In other aspects the feet 24, 30, 32 and 34 may be coated with an anti-slippage material.

Surgical drape supports according to the invention are expected to improve patient comfort and safety during any type of surgery to the head and neck, especially ophthalmic surgery as shown by way of example in this specification. Additional benefits include the ability to manufacture the surgical drape support by "additive" (3-D printing) techniques, which yields an affordable and versatile support which can be readily custom matched to any patient. The ability to invert the support to suit different patients and mount accessories (clips for oxygen lines, etc.) further increases the versatility of the design. The surgical drape support according to the invention may be formed of material, which is easy to sanitize, thereby furthering the economic advantages of the invention.

EXEMPLARY ASPECTS

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: A surgical drape support for positioning on a patient's chest to support a drape above the patient's nose and mouth, the surgical drape support comprising: a main arch defining an inner main surface, an outer main surface, a main crown, a first main base edge, and a second main base edge; a first lower foot extending downward from the first main base edge and away from the outer main surface; and a second lower foot extending downward from the second main base edge and away from the outer main surface; a first upper foot extending upwards and away from the outer main surface to a position above the main crown; and a second upper foot extending upwards and away from the outer main surface to a position above the main crown; wherein when the first lower foot and the second lower foot are positioned on the patient's chest, the first upper foot and the second upper foot are configured to support the drape over the patient's nose and mouth.

Aspect 2: The surgical drape support of aspect 1, wherein when the first upper foot and the second upper foot are positioned on the patient's chest, the first lower foot and the second lower foot are configured to support the drape over the patient's nose and mouth.

Aspect 3: The surgical drape support of any one of aspects 1 and 2, wherein the first lower foot and the second lower foot comprise concave surfaces when they are positioned on the patient's chest.

Aspect 4: The surgical drape support of any one of aspects 1-3, wherein the first upper foot and the second upper foot comprise concave surfaces when they are positioned on the patient's chest.

Aspect 5: The surgical drape support of any one of aspects 1-4, wherein the first lower foot and the second lower foot define a lower foot width; wherein the first upper foot and the second upper foot define an upper foot width; and wherein the upper foot width is smaller than the lower foot width.

Aspect 6: The surgical drape support of aspect 5, wherein lower foot width is between 180 and 220 mm; and wherein the upper foot width is between 118 and 158 mm.

Aspect 7: The surgical drape support of any one of aspects 1-5, wherein the main arch defines a main arch height; and wherein the main arch height is approximately 85 mm.

Aspect 8: The surgical drape support of any one of aspects 1-7, further comprising: at least one accessory attachment feature.

Aspect 9: The surgical drape support of aspect 8, wherein the at least one accessory attachment feature is positioned on the main inner surface.

Aspect 10: The surgical drape support of any one of aspects 8 and 9, wherein the at least one accessory attachment feature comprises an oxygen hose clamp.

Aspect 11: The surgical drape support of any one of aspects 1-10, further comprising at least four accessory pathways, the at least four accessory pathways comprising: a main pathway through the main inner surface; a secondary pathway between the first upper foot and the second upper foot; a first side pathway between the first upper foot and the first lower foot; and a second side pathway between the second upper foot and the second lower foot.

Aspect 12: The surgical drape support of any one of aspects 1-11, wherein the main arch comprises a semi-cylinder.

Aspect 13: The surgical drape support of any one of aspects 1-12, wherein the main arch is concave when the first lower foot and the second lower foot are positioned on the patient's chest; and wherein the main arch is convex when the first upper foot and the second lower foot are positioned on the patient's chest.

Aspect 14: The surgical drape support of any one of aspects 1-13, wherein the main arch comprises: a symmetrical body portion defining a vertical axis; and a front lip portion, the front lip portion tapered downwards at an angle from the vertical axis the first lower foot and second lower foot are positioned on patient's chest.

Aspect 15: The surgical drape support of aspect 14, wherein the front lip portion is angled downward from the vertical axis at an angle of approximately 30 degrees.

Aspect 16: A surgical drape support for positioning on a patient's chest to support a drape above the patient's nose and mouth, the surgical drape support comprising: a main arch defining an inner main surface, an outer main surface, a main crown, a first main base edge, and as second main base edge; a first lower foot extending downward from the first main base edge and away from the outer main surface; and a second lower foot extending downward from the second main base edge and away from the outer main surface, the first lower foot and the second lower foot defining a lower foot width; a first upper foot extending upwards and away from the outer main surface to a position above the main crown; and a second upper foot extending upwards and away from the outer main surface to a position above the main crown, the first upper foot and the second upper foot defining an upper foot width, the upper foot width smaller than the lower foot width; wherein when the first lower foot and the second lower foot are positioned on the patient's chest, the first upper foot and the second upper foot are configured to support the drape over the patient's nose and mouth; wherein when the first upper foot and the second upper foot are positioned on the patient's chest, the first lower foot and the second lower foot are configured to support the drape over the patient's nose and mouth.

Aspect 17: The surgical drape support of aspect 16, wherein the first lower foot and the second lower foot comprise concave surfaces when they are positioned on the patient's chest; and wherein the first upper foot and the second upper foot comprise concave surfaces when they are positioned on the patient's chest.

Aspect 18: The surgical drape support of any one of aspects 16 and 17, wherein lower foot width is between 180 and 220 mm; and wherein the upper foot width is between 118 and 158 mm Aspect 19: The surgical drape support of any one of aspects 16-18, wherein the main arch defines a main arch height; and wherein the main arch height is approximately 85 mm.

Aspect 20: The surgical drape support of any one of aspects 16-19, wherein upper foot width is approximately 70 percent of the lower foot width.

Aspect 21: The surgical drape support of any one of aspects 16-20, further comprising: at least one accessory attachment feature.

Aspect 22: The surgical drape support of aspect 21, wherein the at least one accessory attachment feature is positioned on the main inner surface.

Aspect 23: The surgical drape support of any one of aspects 21-22, wherein the at least one accessory attachment feature comprises an oxygen hose clamp.

Aspect 24: The surgical drape support of any one of aspects 16-23, further comprising at least four accessory pathways, the at least four accessory pathways comprising: a main pathway through the main inner surface; a first side pathway between the first upper foot and the first lower foot; and a second side pathway between the second upper foot and the second lower foot.

Aspect 25: The surgical drape support of any one of aspects 16-24, wherein the main arch comprises a semi-cylinder.

Aspect 26: The surgical drape support of any one of aspects 16-25, wherein the main arch comprises: a symmetrical body portion defining a vertical axis; and a front lip portion, the front lip portion tapered downwards at an angle from the vertical axis the first lower foot and second lower foot are positioned on patient's chest.

Aspect 27: The surgical drape support of aspect 26, wherein the front lip portion is angled downward from the vertical axis at an angle of approximately 30 degrees.

Aspect 28: A method of supporting a surgical drape over a patient comprising: placing a surgical drape support on the patient's chest, the surgical drape support comprising: a main arch defining an inner main surface, an outer main surface, a main crown, a first main base edge, and as second main base edge; a first lower foot extending downward from the first main base edge and away from the outer main surface; and a second lower foot extending downward from the second main base edge and away from the outer main surface, the first lower foot and the second lower foot defining a lower foot width; a first upper foot extending upwards and away from the outer main surface to a position above the main crown; and a second upper foot extending upwards and away from the outer main surface to a position above the main crown, the first upper foot and the second upper foot defining an upper foot width, the upper foot width smaller than the lower foot width; positioning the first lower foot and the second lower foot on the patient's chest such that the surgical drape is positioned over the patient's nose and mouth.

Aspect 29: The method according to aspect 28, further comprising: inverting the surgical drape support such that the first upper foot and the second upper foot are positioned on the patient's chest for smaller patients such that the drape over the patient's nose and mouth.

What is claimed is:

1. A surgical drape support configured for positioning on a patient's chest to support a drape above the patient's nose and mouth, the surgical drape support comprising:
   a main arch defining an inner main surface, an outer main surface, a main crown, a first main base edge, and a second main base edge;
   a first lower foot extending downward from the first main base edge and away from the outer main surface; and
   a second lower foot extending downward from the second main base edge and away from the outer main surface;
   a first upper foot extending upwards and away from the outer main surface to a position above the main crown; and
   a second upper foot extending upwards and away from the outer main surface to a position above the main crown;
   wherein when the first lower foot and the second lower foot are positioned on the patient's chest, the first upper foot and the second upper foot are configured to support the drape over the patient's nose and mouth.

2. The surgical drape support of claim 1, wherein the first lower foot and the second lower foot define a lower foot width;
   wherein the first upper foot and the second upper foot define an upper foot width; and
   wherein the upper foot width is smaller than the lower foot width.

3. The surgical drape support of claim 2, wherein lower foot width is between 180 and 220 mm; and
   wherein the upper foot width is between 118 and 158 mm.

4. The surgical drape support of claim 3, wherein the main arch defines a main arch height; and wherein the main arch height is approximately 85 mm.

5. The surgical drape support of claim 1, further comprising:
   at least one accessory attachment feature.

6. The surgical drape support of claim 5, wherein the at least one accessory attachment feature comprises an oxygen hose clamp.

7. The surgical drape support of claim 1, wherein the main arch comprises:
   a symmetrical body portion defining a vertical axis; and
   a front lip portion, the front lip portion tapered downwards at an angle from the vertical axis when the first lower foot and second lower foot are positioned on patient's chest.

8. The surgical drape support of claim 7, wherein the front lip portion is angled downward from the vertical axis at an angle of 30 degrees.

9. The surgical drape support of claim 1, wherein when the first upper foot and the second upper foot are positioned on the patient's chest, the first lower foot and the second lower foot are configured to support the drape over the patient's nose and mouth.

10. A surgical drape support configured for positioning on a patient's chest to support a drape above the patient's nose and mouth, the surgical drape support comprising:
    a main arch defining an inner main surface, an outer main surface, a main crown, a first main base edge, and as second main base edge;
    a first lower foot extending downward from the first main base edge and away from the outer main surface; and
    a second lower foot extending downward from the second main base edge and away from the outer main surface, the first lower foot and the second lower foot defining a lower foot width;

a first upper foot extending upwards and away from the outer main surface to a position above the main crown; and a second upper foot extending upwards and away from the outer main surface to a position above the main crown, the first upper foot and the second upper foot defining an upper foot width, the upper foot width smaller than the lower foot width;

wherein when the first lower foot and the second lower foot are positioned on the patient's chest, the first upper foot and the second upper foot are configured to support the drape over the patient's nose and mouth;

wherein when the first upper foot and the second upper foot are positioned on the patient's chest, the first lower foot and the second lower foot are configured to support the drape over the patient's nose and mouth.

11. The surgical drape support of claim 10, further comprising:
at least one accessory attachment feature.

12. The surgical drape support of claim 11, wherein the at least one accessory attachment feature comprises an oxygen hose clamp.

13. The surgical drape support of claim 10, wherein the main arch comprises:
a symmetrical body portion defining a vertical axis; and
a front lip portion, the front lip portion tapered downwards at an angle from the vertical axis the first lower foot and second lower foot are positioned on patient's chest.

14. The surgical drape support of claim 13, wherein the front lip portion is angled downward from the vertical axis at an angle of 30 degrees.

15. The surgical drape support of claim 10, wherein the first lower foot and the second lower foot comprise concave surfaces; and
wherein the first upper foot and the second upper foot comprise concave surfaces.

16. The surgical drape support of claim 10, wherein lower foot width is between 180 and 220 mm; and
wherein the upper foot width is between 118 and 158 mm.

17. The surgical drape support of claim 10, wherein the upper foot width is 70 percent of the lower foot width.

18. The surgical drape support of claim 10, wherein the main arch comprises a semi-cylinder.

19. A method of supporting a surgical drape over a patient comprising:
placing a surgical drape support on the patient's chest, the surgical drape support comprising:
a main arch defining an inner main surface, an outer main surface, a main crown, a first main base edge, and a second main base edge;
a first lower foot extending downward from the first main base edge and away from the outer main surface;
a second lower foot extending downward from the second main base edge and away from the outer main surface, the first lower foot and the second lower foot defining a lower foot width;
a first upper foot extending upwards and away from the outer main surface to a position above the main crown; and
a second upper foot extending upwards and away from the outer main surface to a position above the main crown, the first upper foot and the second upper foot defining an upper foot width, the upper foot width smaller than the lower foot width; and
positioning the first lower foot and the second lower foot on the patient's chest such that the surgical drape is positioned over the patient's nose and mouth.

20. The method according to claim 19, further comprising: inverting the surgical drape support such that the first upper foot and the second upper foot are positioned on the patient's chest for smaller patients such that the drape over the patient's nose and mouth.

\* \* \* \* \*